United States Patent
Nielsen

(10) Patent No.: US 10,596,329 B2
(45) Date of Patent: Mar. 24, 2020

(54) TORSION SPRING DRIVEN INJECTION DEVICE

(71) Applicant: Novo Nordisk A/S, Bagsvaerd (DK)

(72) Inventor: Christian Hoejris Nielsen, Copenhagen NV (DK)

(73) Assignee: Novo Nordisk A/S, Bagsvaerd (DK)

(*) Notice: Subject to any disclaimer, the term of this patent is extended or adjusted under 35 U.S.C. 154(b) by 527 days.

(21) Appl. No.: 15/509,899

(22) PCT Filed: Sep. 14, 2015

(86) PCT No.: PCT/EP2015/070910
§ 371 (c)(1),
(2) Date: Mar. 9, 2017

(87) PCT Pub. No.: WO2016/041883
PCT Pub. Date: Mar. 24, 2016

(65) Prior Publication Data
US 2017/0259011 A1    Sep. 14, 2017

(30) Foreign Application Priority Data
Sep. 15, 2014 (EP) ................... 14184702

(51) Int. Cl.
*A61M 5/32* (2006.01)
*A61M 5/20* (2006.01)
*A61M 5/315* (2006.01)

(52) U.S. Cl.
CPC ........ *A61M 5/3245* (2013.01); *A61M 5/20* (2013.01); *A61M 5/3158* (2013.01);
(Continued)

(58) Field of Classification Search
CPC ................. A61M 2005/208; A61M 5/3245
See application file for complete search history.

(56) References Cited

U.S. PATENT DOCUMENTS

| 8,096,978 B2 | 1/2012 | Markussen |
| 8,758,304 B2 | 6/2014 | Kemp et al. |

(Continued)

FOREIGN PATENT DOCUMENTS

| EP | 2438941 A1 | 4/2012 |
| JP | 2013539680 A | 10/2013 |

(Continued)

*Primary Examiner* — Nathan R Price
*Assistant Examiner* — John A Doubrava
(74) *Attorney, Agent, or Firm* — Wesley Nicolas

(57) ABSTRACT

The present invention relates to a torsion spring driven injection device for delivering set doses of a liquid drug. The injection device mechanism is encapsulated in a housing which also stores the cartridge containing the liquid drug. A needle cannula which is in liquid communication with the interior of the cartridge and which has a distal tip is shielded by a telescopically movable needle shield is used to inject the set dose. The needle cannula is preferably used for multiple injections and cleaned between subsequent injections. The drive mechanism further comprises a nut member engaging the piston rod and releasable coupled to the housing to operate as a pressure relief mechanism. The telescopically movable needle shield covering the distal tip of the needle cannula is formed to lock the nut member to the housing during injection.

16 Claims, 8 Drawing Sheets

(52) U.S. Cl.
CPC .... *A61M 5/31553* (2013.01); *A61M 5/31563* (2013.01); *A61M 5/31585* (2013.01); *A61M 5/31593* (2013.01); *A61M 2005/208* (2013.01); *A61M 2005/2026* (2013.01); *A61M 2005/2073* (2013.01)

(56) References Cited

U.S. PATENT DOCUMENTS

| | | | | |
|---|---|---|---|---|
| 2005/0261634 | A1* | 11/2005 | Karlsson | A61M 5/20 604/197 |
| 2007/0021718 | A1 | 1/2007 | Burren et al. | |
| 2015/0174335 | A1* | 6/2015 | Roervig | A61M 5/20 604/198 |

FOREIGN PATENT DOCUMENTS

| | | | |
|---|---|---|---|
| WO | 2007131025 | A1 | 11/2007 |
| WO | 2011003979 | A1 | 1/2011 |
| WO | 2011/109205 | A2 | 9/2011 |
| WO | 2012067582 | A1 | 5/2012 |
| WO | 2012128699 | A1 | 9/2012 |
| WO | 2014001318 | A2 | 1/2014 |
| WO | 2014001319 | A1 | 1/2014 |
| WO | 2014060369 | A1 | 4/2014 |

* cited by examiner

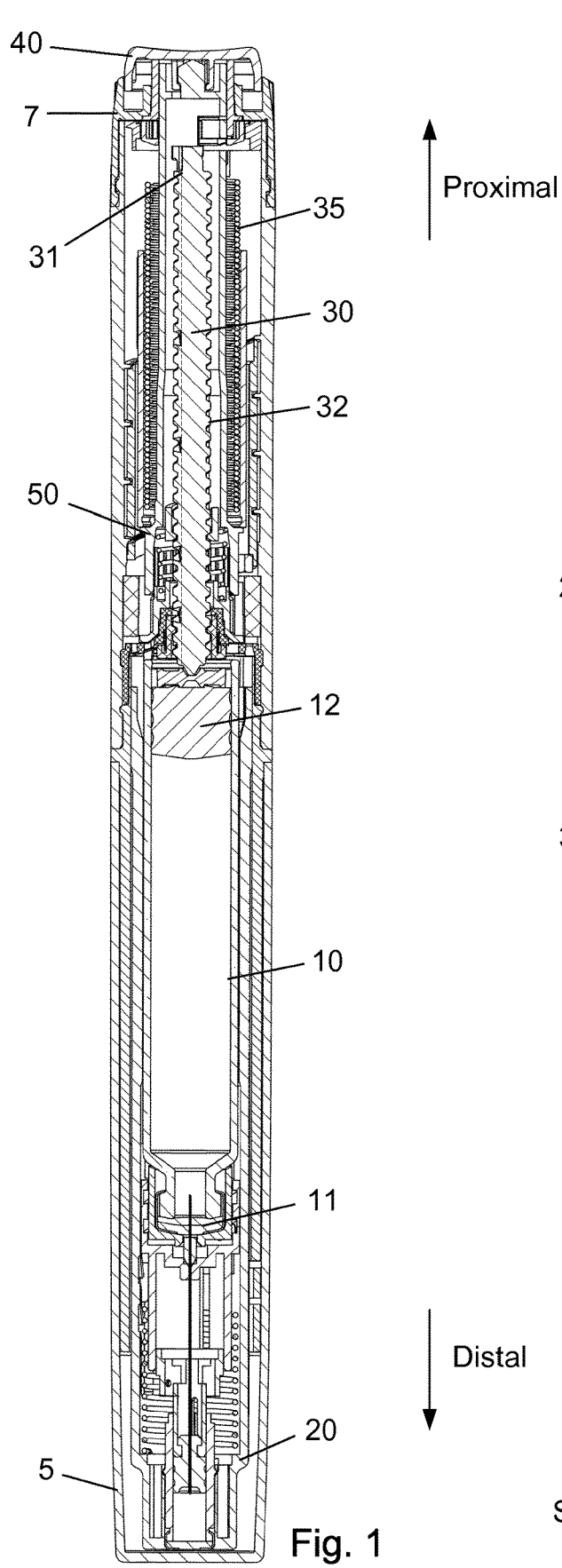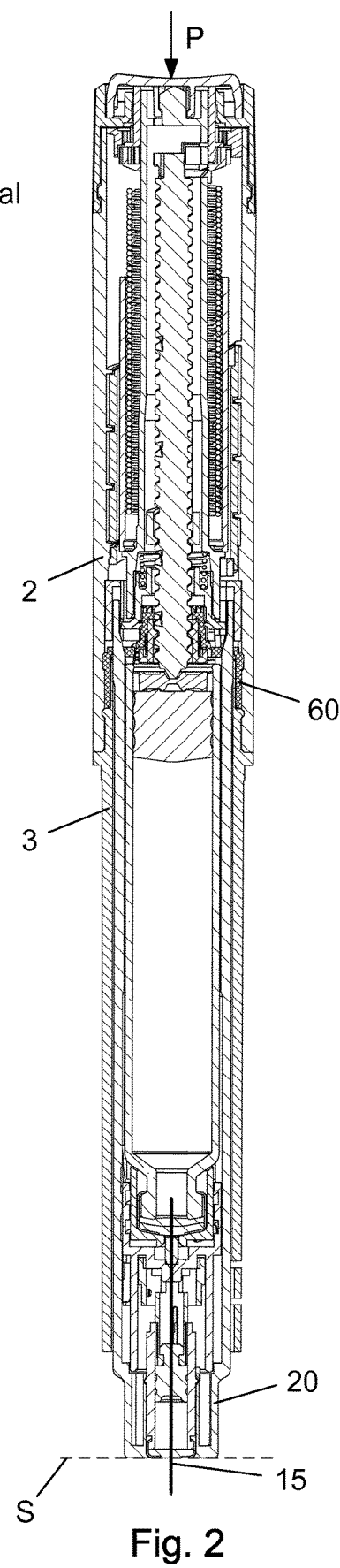

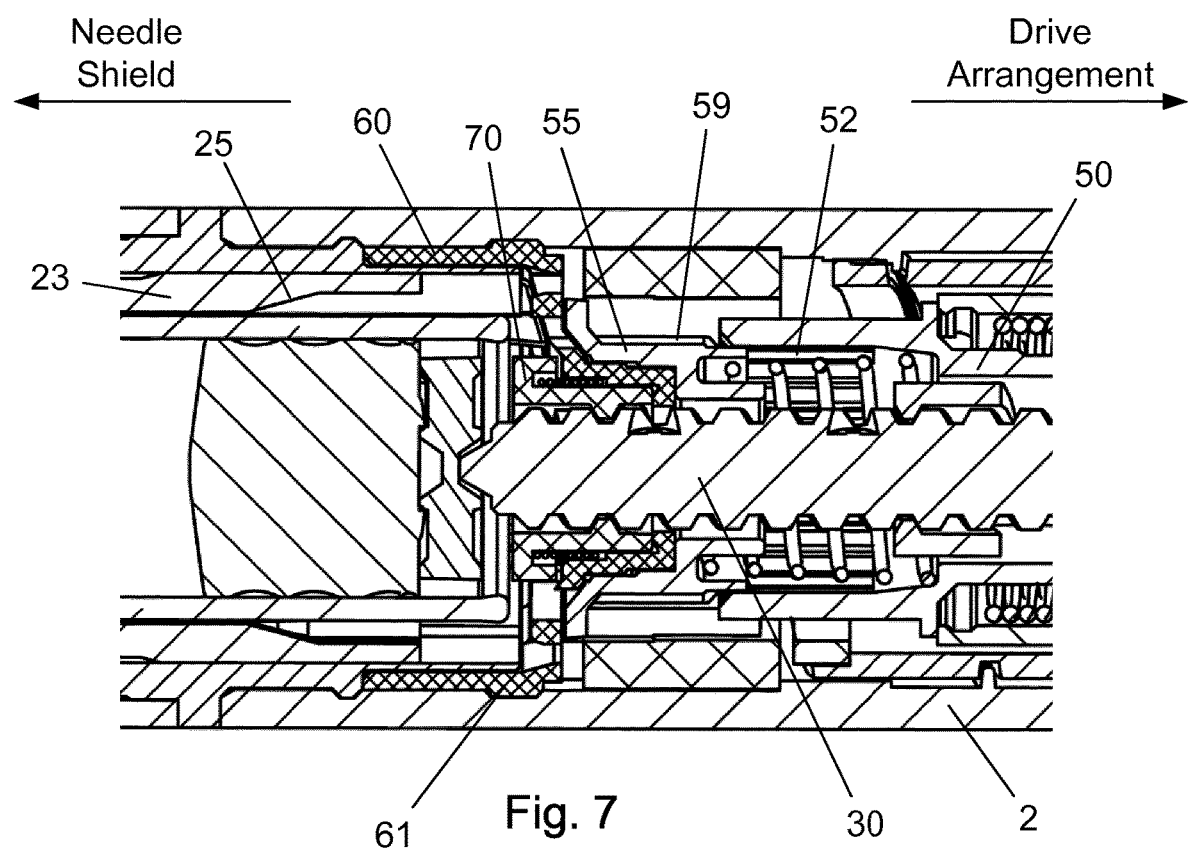
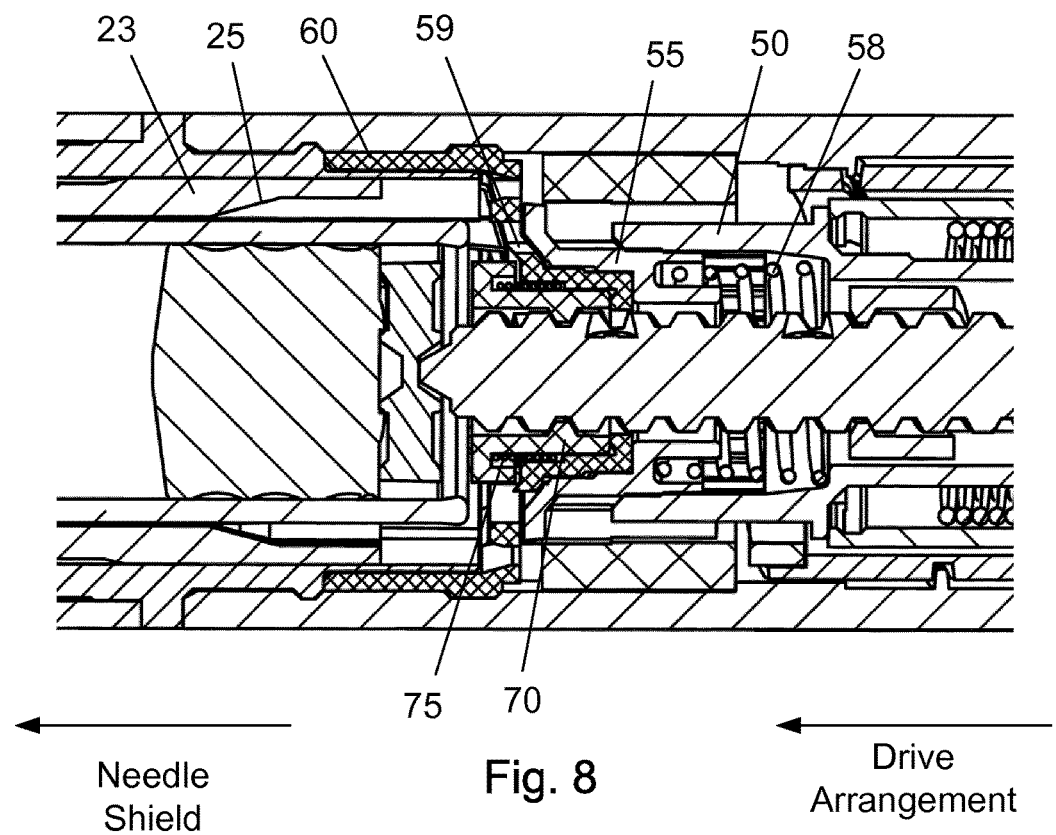

TORSION SPRING DRIVEN INJECTION DEVICE

CROSS-REFERENCE TO RELATED APPLICATIONS

This application is a 35 U.S.C. § 371 National Stage application of International Application PCT/EP2015/070910 (published as WO 2016/041883), filed Sep.14, 2015, which claims priority to European Patent Application 14184702.0, filed Sep. 15, 2014, the contents thereof which are incorporated by reference in their entirety.

THE TECHNICAL FIELD OF THE INVENTION

The invention relates to a torsion spring driven injection device for automatically expelling individually set doses of a liquid drug. It especial relates to such automatic injection device having both a shielded needle cannula and an injection button. In particular it relates to a pressure relief mechanism allowing for expansion of a liquid drug contained in the injection device. The invention further relates to a release mechanism requiring both the activation of the telescopically movable needle shield and manipulation of the injection button in order to perform an injection.

DESCRIPTION OF RELATED ART

WO 2014/001318 discloses a torsion spring driven injection. The injection is driven by a torsion spring which is not strained during dose setting. In order to release the strained spring and execute the automatic injection thetelescopically movable needle shield must be moved axially to activate the release mechanism.

Further, different mechanisms to automatically relief a high pressure in the cartridge of a torsion spring driven injection device is disclosed in WO 2014/060369. In this torsion spring driven injection device the nut engaging the piston rod is constantly fixed to the housing and the rotatable drive member rotating the piston rod is releasable coupled to a clutch element. This clutch element can be activated to engage the drive member by pushing back the telescopically movable needle shield.

It is however rather complicated to operate an axially movable clutch element.

DESCRIPTION OF THE INVENTION

It is an object of the present invention to provide a torsion spring driven injection device having a shielded needle cannula and a more simple pressure release mechanism wherein the piston rod can move freely to automatically relief any exceeding pressure inside the cartridge.

The invention is defined in claim 1. Accordingly, in one aspect the present invention relates to a torsion spring driven injection device for delivering set doses of a liquid drug.

Such torsion spring driven injection device comprises:
- a housing which stores a cartridge containing the liquid drug to be injected. The housing forms the outer barrier of the injection device and can be moulded as one unitary part or be assembled from different parts. Most commonly, the housing is made up from an upper housing connected to a cartridge-holder securing the cartridge.
- a needle cannula in liquid communication with the interior of the cartridge and having a distal tip shielded by a telescopically movable needle shield. The telescopically movable needle shield is axially movable from a first position in which the needle shield is extended to cover the distal tip of the needle cannula to a second position in which the needle shield is retracted to expose the distal tip of the needle cannula,
- a piston rod having a threaded outer surface and a not circular cross-section. The not circular cross-section can be materialized in many different ways, e.g. by providing the piston rod with one or more longitudinal tracks. The piston rod drives a plunger forward inside the cartridge during dose expelling to press out liquid drug through the lumen of the needle cannula.
- a rotatable dose setting member by which a user can set a dose to be injected.
- a torsion spring which is strainable in response to the user rotating the dose setting member and releasable to drive the piston rod. As the user rotates the dose setting member the torsion spring is strained i.e. a torque is build up in the torsion spring. It is however also possible for the user to rotate the dose setting member in the opposite direction to unstrain the torsion spring.
- a user operable injection button which a user can activate to release the torque build up in the torsion spring.
- A rotatable drive member mating the not circular cross-section of the piston rod or having an inner thread mating the outer thread of the piston rod.
- A nut member releasable coupled to the housing and having an inner thread mating the outer thread of the piston rod or having a cross-section mating the not circular cross-section of the piston rod, such that the piston rod is moved axially in the housing upon rotation of the drive member relatively to the housing.

Since the nut member is releasable coupled to the housing it is possible either to lock the nut member to the housing or to release the nut member from the housing. Since the piston rod is engaged to the nut member, the nut member needs to be secured in order to bring the piston rod forward. It is thus necessary to lock the nut member to the housing during expelling of a set dose. The locking of the nut member to the housing is done in response to telescopically movement of the telescopically movable needle shield from the first extended position to the second retracted position.

When the shield is in the first extended position, the nut member is thus free to rotate. Since the nut member can rotate freely, the piston rod engaging the nut member is also free to move. When the injection device is under storage any change in the volume of the liquid drug will move the plunger inside the cartridge. This can thus be done without building up pressure inside the cartridge since the nut member and consequently the piston rod is free to rotate.

In order to secure the nut member to the housing during expelling of the set dose a plurality of radially working arms are preferably provided. These arms are able to be pressed inwardly towards the center line of the injection device thus gripping around the nut member. The radially working arms can be formed directly in the housing or alternatively in a separate part coupled to the housing. This can be beneficial for assembly of the injection device. In one embodiment these radially working arms are provided in a nut holder which is secured to the housing.

The radially working arms are preferably operated by telescopically movement of the telescopically movable needle shield. During injection the user pushes the distal end of the shield against the skin thus moving the shield proximally. This movement from the first position and into the second position is utilized to activate the radially working arms to lock and secure the nut member to the nut holder (or alternatively to the housing).

In one embodiment, a second torsion spring can be encompassed between the nut member and the housing. This second torsion spring is strained during rotation of the nut member which occurs when the plunger of cartridge wander in the proximal direction. Should the plunger afterwards wander back in the distal direction, the torque stored in this torsion spring will rotate the nut member and thus bring the piston rod forward such that the piston rod always abuts the plunger of the cartridge e.g. with a piston rod foot or washer located between the piston rod and the plunger of the cartridge.

This second torsion spring of the pressure relief system can in one example be pretensed such that the a little torque is a present on the nut member thus urging a rotational force onto the piston rod thereby securing abutment with the plunger.

The primary torsion spring is at one end connected to the housing and at the opposite end connected to a drive arrangement. Since the torsion spring is strained during dose setting, the torque stored in the torsion spring will rotate the drive arrangement once the torque is released. The primary torsion spring of the injection device can also be pretensed such that a sufficient torque is always available, also when dosing small doses.

The drive arrangement is further adapted to rotate the rotatable drive member under influence of the torque of the torsion spring. The connection between the drive arrangement and the drive member is however releasable such that the drive member only rotates once it is coupled to the drive arrangement.

In one embodiment, the drive arrangement is coupled to the injection button such that the drive arrangement follows axial movement of the injection button. The connection between the drive arrangement and the injection button is preferably made such that the injection button is rotatable in relation to the drive arrangement.

The drive member is further made such that the drive member can be coupled to the housing or uncoupled from the housing. In one embodiment, the drive member is made engageable/disengageable with the nut holder which again is coupled to the housing. The drive member is thereby either engaged to the housing or disengaged from the housing. In the disengaged position, the drive member is free to rotate whereas in the engaged position it is renderer inrotatable as it is locked to the housing (e.g. via the nut holder).

The engagement between the drive member and the housing is preferably made such that the drive member is axially movable to disengage from the housing. The movement of the drive member is further axially linked to the telescopically movable needle shield such that the drive member is movable out of engagement with the housing upon movement of the telescopically movable needle shield from the first position to the second position. When the user of the injection device then pushes the distal end of the shield against the shield, the proximal movement of the shield releases the drive member from its engagement with the housing such that the drive member is free to rotate when the shield is activated.

At the opposite end of the injection device, the injection button is linked to the drive arrangement such the drive arrangement is axially movable in relation to the housing from a third position to a fourth position upon axial movement of the injection button.

In the third position which is the position in which the injection button is not activated, the drive arrangement is urged proximally e.g. by a compression spring preferably encompassed between the drive member and the drive arrangement. In this position, the drive arrangement is coupled to the housing and thus kept inrotatable.

When a user rotates the dose setting button in this third position, the torsion spring is strained and a torque is build up in the windings of the torsion spring.

To eject the set dose the user pushes the injection button which directly moves the drive arrangement in the distal direction into the fourth position. In this fourth position, the drive arrangement is released from the housing and is solely under the control of the torsion spring which is encompassed between the housing and the drive arrangement. The result being that the torque in the torsion spring is released and potentially rotates the drive arrangement.

Also in this fourth position, the drive arrangement couples to the drive member which is thus able to rotate. However, rotation of the drive member requires that the drive member is disengaged from the housing which again requires that the shield has been moved proximally to its second retracted position.

In order to eject a dose, the user therefore has both to activate the shield and to push the injection button. The sequence in which these two operations are performed has no influence. The set dose is only expelled if the user performs both operations at the same time. Many times the user will choose to push the shield towards the skin which also penetrates the distal tip of the needle cannula through the skin where after the user pushes the injection button and the injection will be performed.

Active rotation of the rotatable drive member by the torsion spring thus requires;
- the telescopically movable needle shield to be in the second position thus releasing the rotatable drive member from the housing, and
- the drive arrangement to be in the fourth position thus releasing the drive arrangement from the housing and delivering the torque of the torsion spring to the rotational drive member via the drive arrangement.

The torsion spring driven injection device herein described is preferably the type which has a cleaning reservoir carried by the telescopically movable needle shield such that the distal tip of the needle cannula is cleaned between subsequent injections such that the same needle cannula can be used for multiple injections. When such telescopically movable needle shield carrying a cleaning reservoir is encompassed in a prefilled injection device, the one and same needle cannula is preferably used to inject the entire content of the prefilled injection device where after both the prefilled injection device and the needle cannula is discarded together. The needle cannula is preferably, but not necessarily permanent connected to the prefilled injection device.

In a further aspect the torsion spring driven injection devices requires simultaneously activation of both the injection member and the shield in order to release the torsion spring and drive an ejection of the set dose. Accordingly in one example, the torsion spring driven injection device can be characterized as below.

EXAMPLE A

A torsion spring driven injection device for delivering set doses of a liquid drug, comprising:

an outer housing storing a cartridge containing the liquid drug, a needle cannula in liquid communication with the interior of the cartridge and having a distal tip shielded by a telescopically movable needle shield, a piston rod for driving the liquid drug out from the cartridge through the needle cannula, a torsion spring which is strainable to set a dose and released to drive the piston rod, and a user operable injection button, and wherein;

release of the torsion spring and driving of the piston rod requires activation of both the needle shield and the injection button.

EXAMPLE B

A torsion spring driven injection device according to example A, wherein the piston rod has a threaded outer surface and a not circular cross-section, and further comprises;

A rotatable drive member mating the not circular cross-section of the piston rod or having an inner thread mating the outer thread of the piston rod, and A nut member coupled to the housing and having an inner thread mating the outer thread of the piston rod or having a cross-section mating the not circular cross-section of the piston rod, such that the piston rod is moved axially in the housing when the drive member is rotated relatively to the housing.

EXAMPLE C

A torsion spring driven injection device according to example B, wherein the strainable torsion spring is encompassed between the housing and a drive arrangement, which drive arrangement is adapted to rotate the rotatable drive member under influence of the torque of the torsion spring.

EXAMPLE D

A torsion spring driven injection device according to example C, wherein the drive arrangement is axially movable in relation to the housing upon activation of the injection button.

EXAMPLE E

A torsion spring driven injection device according to example D, wherein the drive member in a dose setting mode is rotational locked to hinder rotation of the drive member and in a dose ejection mode is unlocked to allow rotation of the drive member under influence of the torque of the torsion spring, and wherein the shift from the dose setting mode to the dose ejection mode requires activation of both the telescopically movable needle shield and the axially movable drive arrangement.

EXAMPLE F

A torsion spring driven injection device according to any of the examples A to F, wherein the telescopically movable needle shield is axially movable from a first position in which the needle shield is extended to cover the distal tip of the needle cannula to a second position in which the needle shield is retracted to expose the distal tip of the needle cannula.

EXAMPLE G

A torsion spring driven injection device according to example F, wherein the telescopically movable needle shield upon axial movement into the second retracted position unlocks the rotatable drive member from the housing.

EXAMPLE H

A torsion spring driven injection device according to any of the examples C to G, wherein the axially movable drive arrangement is movable from a third position to a fourth position upon activation of the injection button.

EXAMPLE I

A torsion spring driven injection device according to example H, wherein the drive arrangement in the third position is decoupled from the drive member and coupled to the housing.

EXAMPLE J

A torsion spring driven injection device according to any of the examples H and I, wherein the drive arrangement in the fourth position is coupled to the drive member and decoupled from the housing.

EXAMPLE K

A torsion spring driven injection device according to any of the examples H to J, wherein rotation of the rotatable drive member by the torsion spring requires;

the telescopically movable needle shield to be in the second position thus releasing the rotatable drive member from the housing, and the drive arrangement to be in the fourth position thus delivering the torque of the torsion spring to the rotational drive member via the drive arrangement.

EXAMPLE L

A torsion spring driven injection device according to any of the examples B to K, wherein the nut member is releasable coupled to the housing.

EXAMPLE M

A torsion spring driven injection device according to example L, wherein the telescopically movable needle shield locks the nut member to the housing upon telescopically movement of the needle shield from the first extended position to the second retracted position.

EXAMPLE N

A torsion spring driven injection device according to example M, wherein a torsion spring is encompassed between the nut member and the housing.

Definitions

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

The term "Needle Cannula" is used to describe the actual conduit performing the penetration of the skin during injection. A needle cannula is usually made from a metallic material such as e.g. stainless steel, but could also be made from a polymeric material or a glass material.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS:

The present invention will become more fully understood from the detailed description given below in connection with a preferred embodiment and with reference to the drawings which are given by way of illustration only, and thus, are not limitive of the present invention, and wherein:

FIG. 1 show a cross sectional view of the injection device in a dose setting position.

FIG. 2 show a cross sectional view of the injection device during injection.

FIG. 7 show a cross sectional view of the drive mechanism in the dose setting position.

FIG. 8 show a cross sectional view of the drive mechanism with the injection button pressed down.

The figures are schematic and simplified for clarity, and they just show details, which are essential for the understanding of the present invention, while other details are left out. Throughout, the detailed description, the same reference numerals are used for identical or corresponding parts.

DETAILED DESCRIPTION OF EMBODIMENT

Figure 3:
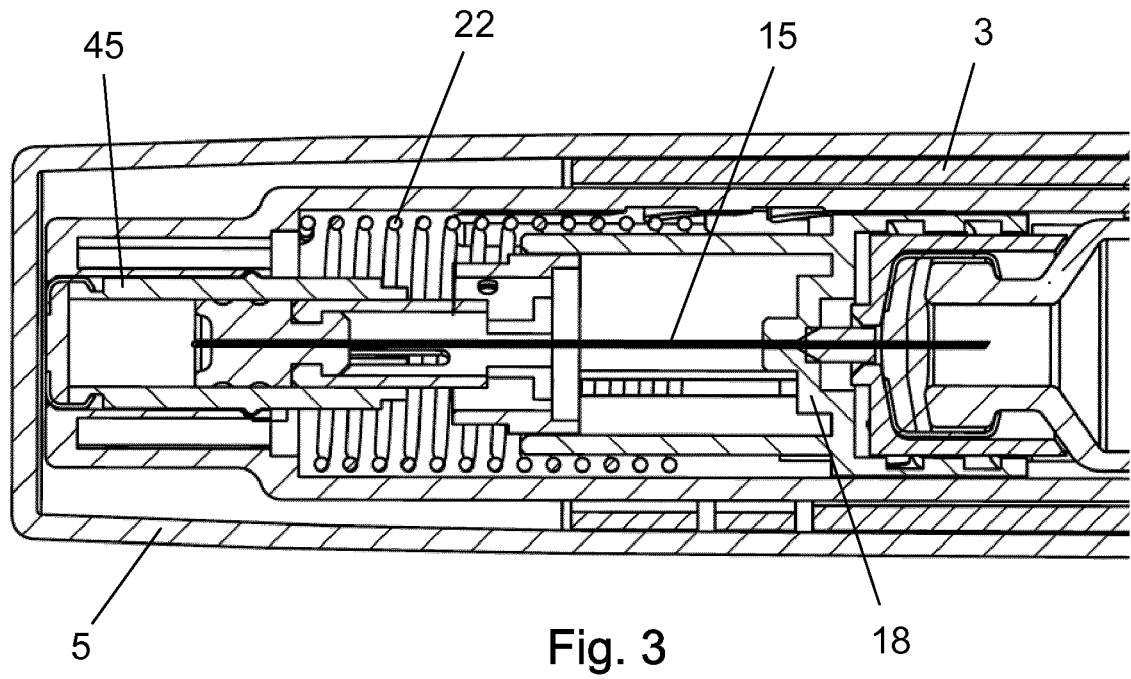
FIG. 3 show an enlarged cross sectional view of the distal end of the injection device of FIG. 1

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and carrying the dose dial button as depictured in FIG. 1. "Distal" and "proximal" are meant to be along an axial orientation extending along the longitudinal axis of the injection device and is further indicated in the figures.

FIG. 1-2 discloses a torsion spring driven injection device 1 according to the invention. The main components of the injection device 1 are:

A cartridge 10 containing the liquid drug to be injected,
A needle cannula 15 which is in liquid communication with the interior of the cartridge 10,
A telescopically movable needle shield 20 for covering at least part of the needle cannula 15 between injections,
A piston rod 30 for driving the liquid drug out from the cartridge 10,
A torsion spring 35 which is strainable by a user when rotating a rotatable dose setting member 7,
A user operable injection button 40 located at a proximal end.

The cartridge 10 is usually made from glass and has a distal end which is closed by a septum 11. The proximal end is closed by a movable plunger 12 which is moved forward by the piston rod 40 during injection. The interior confinement between the septum 11 and the plunger 12 contains the liquid drug.

The cartridge 10 is secured in a housing 2 by a cartridge holder 3 such that the housing 2 and the cartridge holder 3 together form the outer housing 2, 3 of the injection device 1. The housing 2 and the cartridge holder 3 could also be moulded as one unitary housing.

To move the plunger 12 forward inside the cartridge 10, a piston rod 30 is provided which piston rod 30 has a not circular cross-section by being provided with a longitudinal groove 31 and a helical thread 32 on the outside surface. Between the piston rod 30 and the plunger 12, a piston rod foot or washer 33 can be provided to better distribute the force to the movable plunger 12.

Figure 4:
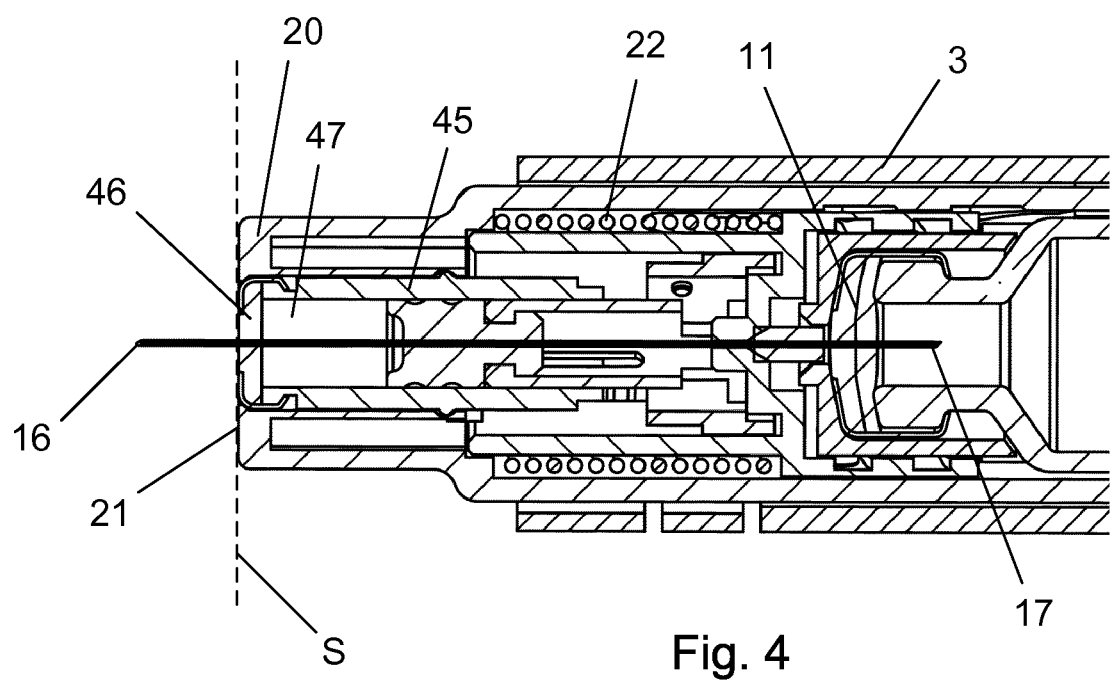
FIG. 4 show an enlarged cross sectional view of the distal end of invention device of FIG. 2.

An expanded view of the distal end of the injection device 1 is shown in FIG. 3-4. The needle cannula 15 has a distal tip 16 for penetrating into a user and a proximal end 17 which is inserted into the cartridge 10 such that liquid drug can flow through the needle cannula 15 and into the user. The needle cannula 15 is anchored in a hub 18 which in this embodiment is permanently secured to the remaining part of the injection device 1 such that the needle cannula 15 cannot be removed.

The telescopically movable needle shield 20 is distally provided with a cleaning unit 45 for cleaning at least the distal tip 16 of the needle cannula 15 between injections. Such cleaning unit 45 is described in WO 2015/062845 and is distally provided with a distal membrane 46 through which the distal tip 16 of the needle cannula 15 penetrates during injection. Adjacent and proximal to this membrane 46 a chamber 47 is provided which chamber 47 contains a liquid cleaning agent. This cleaning agent can be any kind of cleaning agent, however in a preferred embodiment; the cleaning agent is identical to the preservative solvent contained in the liquid drug, or simply to the liquid drug itself. In this way, the liquid drug in the cartridge 10 is not contaminated should some of the cleaning agent flow back through the lumen of the needle cannula 15.

Whenever the user performs an injection as disclosed in FIG. 4 the user presses the distal end 21 of the telescopically movable needle shield 20 against the skin S which operates the telescopically movable needle shield 20 and the cleaning unit 45 in the proximal direction such that the distal tip 16 of the needle cannula 15 protrudes beyond the needle shield 20 and penetrates into the skin S of the user.

Following an injection when the needle shield 20 is removed from the skin S, a compression spring 22 provided between the hub 18 and the needle shield 20 moves the needle shield 20 in a distal direction to the position depicted in FIG. 3 where it can be seen that the distal tip 16 of the needle cannula 15 is moved back into the liquid cleaning agent in the cleaning chamber 47 of the cleaning unit 45.

Figure 14:
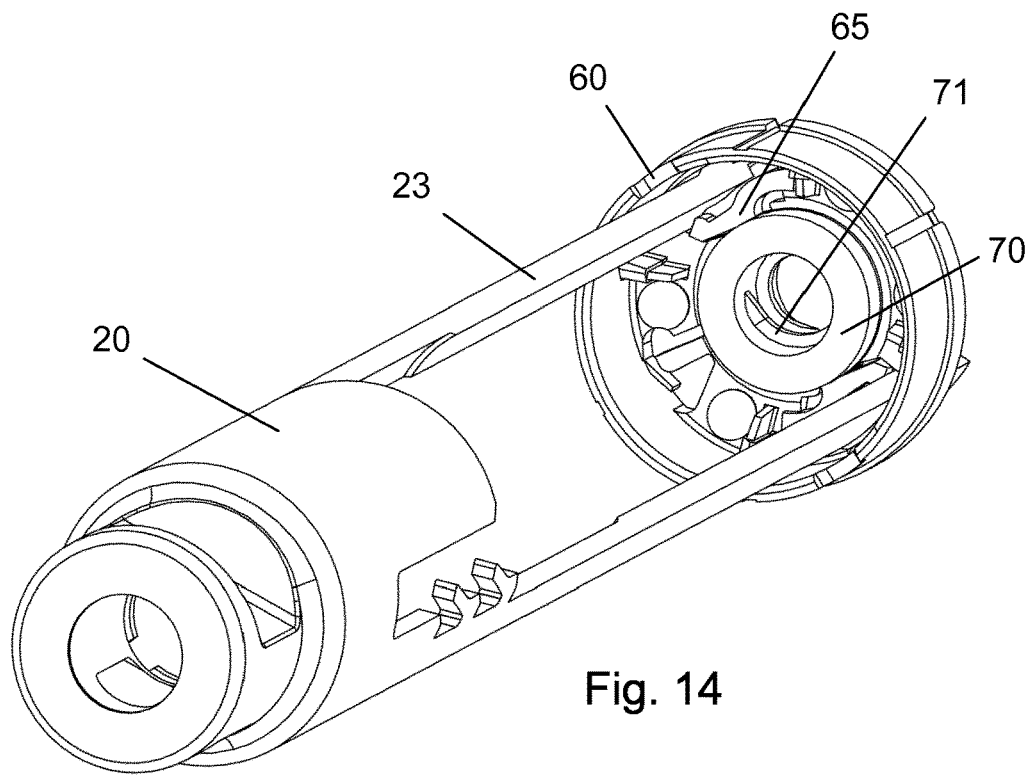
FIG. 14 show a perspective view of the telescopically movable needle shield viewed from a distal position.

The needle shield 20 which is thus telescopically movable against the bias of the compression spring 22 is proximally provided with a number of arms 23. In the exemplary embodiment there are two such arms 23, the use of which will be explained later. The telescopically movable needle shield 20 and the arms 23 is disclosed in details in FIG. 14-15 which also discloses that each arm 23 at the proximal end has a step 24 and a ramp 25.

The injection button 40 is provided at a proximal end of the injection device 1 as disclosed in FIG. 1-2. FIG. 1 depicts the injection device 1 in a state of rest (the dose setting mode) and FIG. 2 depicts the injection device 1 with the injection button 40 pressed down (dose injection mode) which is usually done by the user applying a pressure P to the proximal end of the injection button 40 preferably by use of a finger.

Figure 5:
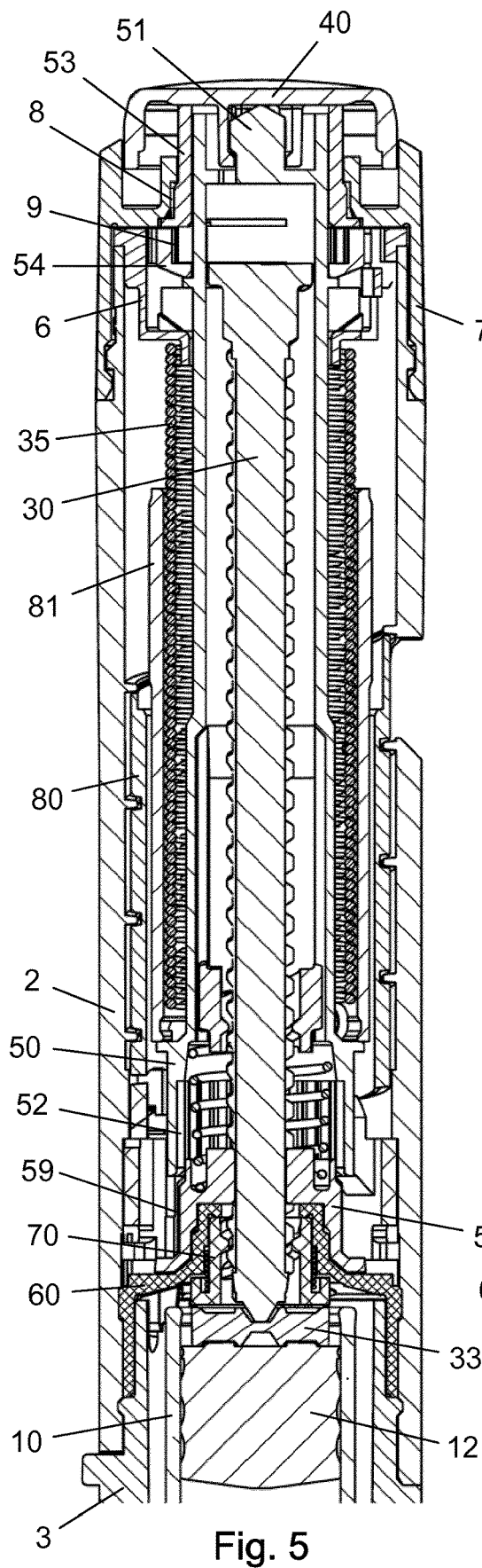
FIG. 5 show an enlarged cross sectional view of the proximal end of the injection device of FIG. 1.

FIG. 5 discloses an enlarged view of the proximal half end of the injection deice 1 in the same state of rest as in FIG. 1. However, viewed in a different cross-sectional direction.

Figure 6:
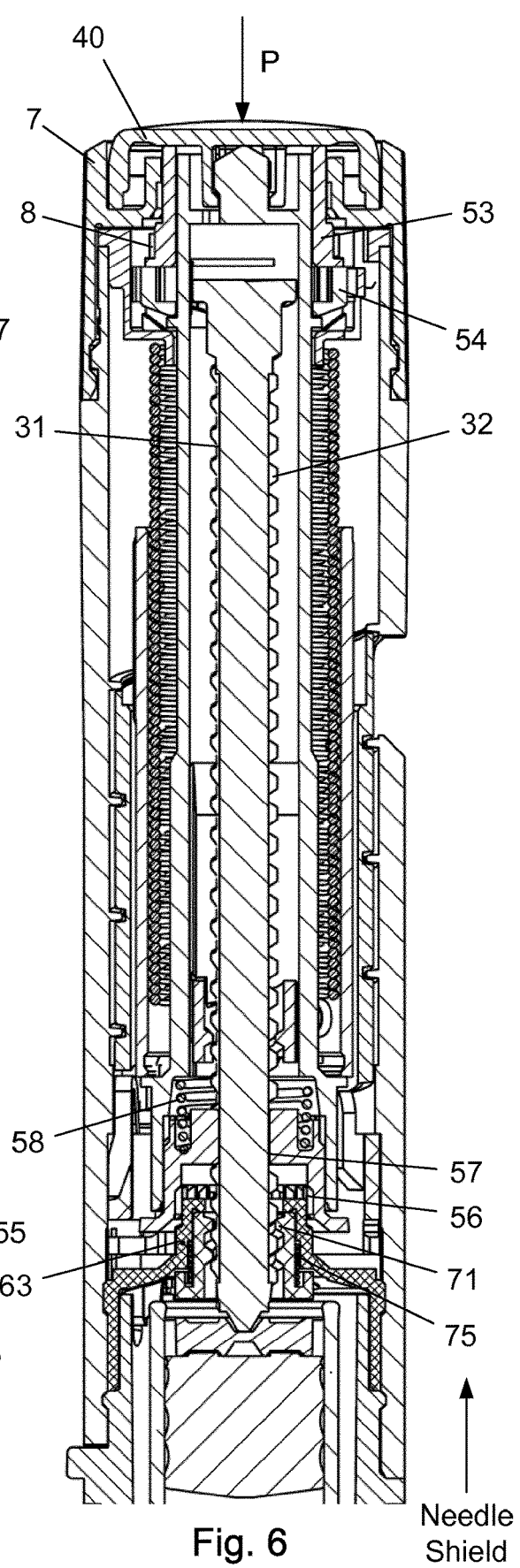
FIG. 6 show an enlarged cross sectional view of the proximal end of the injection device of FIG. 2.

FIG. 6 also depicts an enlarged view of the proximal half end of the injection device 1. This view is in the same injection state as in FIG. 2, but also viewed in a different cross-sectional direction.

The injection button 40 is stiffly connected to a drive arrangement 50 via a click protrusion 51 allowing the injection button 40 to rotate relatively to the drive arrangement 50. The drive arrangement 50 is distally connected with the torsion spring 35. Proximally, the torsion spring 35 is secured to the housing 2 via a spring base 6. The spring base 6 is inrotatable secured to housing or alternatively moulded as an integral part of the housing 2.

The housing 2 is further proximally provided with a dose dial 7 which is rotatable mounted to the housing 2 and further connected to the drive arrangement 50 via an axial releasable coupling 8. The coupling 8 is provided between an intermediate part 53 inrotatable coupled to the drive arrangement 50 and axially coupled to injection button 40. When a user rotates the dose dial 7 to set a dose to be injected, the drive arrangement 50 rotate together with the dose dial 7 and the torsion spring 35 is twisted and thus strained.

When a user pushes the injection button 40 in the distal direction (indicated by the arrow "P" in FIG. 2 and FIG. 6), the intermediate member 53 move axially together with the drive arrangement 50 which releases the coupling 8 as depicted in FIG. 6 and thus disconnects the drive arrangement 50 from the dose dial 7 such that the torsion spring 35 can rotate the drive arrangement 50.

The drive arrangement 50 further has an outer element 81 carrying a scale drum 80. The scale drum 80 is coupled to the outer element 81 in an axial movable way and is further threaded to the housing 2 such that the scale drum 80 move helically away form a zero position during dose setting and move helically back to the zero position during injection.

A ratchet mechanism 9 is preferably provided between the spring base 6 and the drive arrangement 50. A ratchet arm carried on the drive arrangement 50 engages a toothed ring on a tooth element 54. This tooth element 54 is mounted inside the spring base 6 and is axially slidable with the drive arrangement 50. In the dose setting position disclosed in FIG. 5, the tooth element 54 is rotatable secured to the spring base 6 such that the ratchet arm clicks over the teeth inside the tooth element 54 as the torsion spring 35 is strained i.e. when the drive arrangement 50 is rotated. In the dose expelling position depicted in FIG. 6, the tooth element 54 has been moved axially out of this engagement thus allowing the tooth element 54 to rotate with the drive arrangement 50. The engagement between the ratchet arm of the drive arrangement 50 and the teeth of the tooth element 54 is shaped such the ratchet mechanism 9 holds the torque stored in torsion spring 35 upon rotation of the dose dial 7 i.e. during setting of the dose. When the injection button 40 is pushed in a distal direction during expelling of the set dose, the ratchet mechanism 9 is released to allow rotation of the drive arrangement 50.

Further a different release mechanism can be provided such that the ratchet arm can be released when dialling the dose dial 7 in an opposite direction thus allowing a set dose to be lowered. Such second release mechanism would preferably be an element forcing the ratchet arm carried by the drive arrangement 50 out of its engagement with the teeth of the tooth element 54 during dial down as is well-known in the art.

In the state of rest disclosed in FIG. 1 and FIG. 5 the needle shield 20 is located in its distally extended position covering the distal tip 16 of the needle cannula 15 and the injection button 40 with the drive arrangement is located in its proximal position.

In order to perform an injection the needle shield 20 is moved proximally such that the proximal extending arms 23 engage and moves a drive member 55 proximally, preferably via the steps 24 (depicted in FIGS. 10 and 15) which engages an outwardly pointing flange on the drive member 55. At the same time the distal movement of the injection button 40 and the drive arrangement 50 moves the drive arrangement 50 into engagement with the same drive member 55 as will be explained in the following. FIG. 2 and FIG. 6 depicts the situation in which the injection button 40 is pressed and the needle shield 20 is urged proximally i.e. a situation in which the set dose is expelled.

The drive mechanism itself is disclosed in a further enlarged version in the FIGS. 7, 8, 9 and 10. In the exemplary embodiment, the drive mechanism comprises a nut holder 60 which is both axially and rotational secured in the housing 2. Alternatively, the nut holder 60 can be moulded as an integral part of the housing 2.

Figure 11:
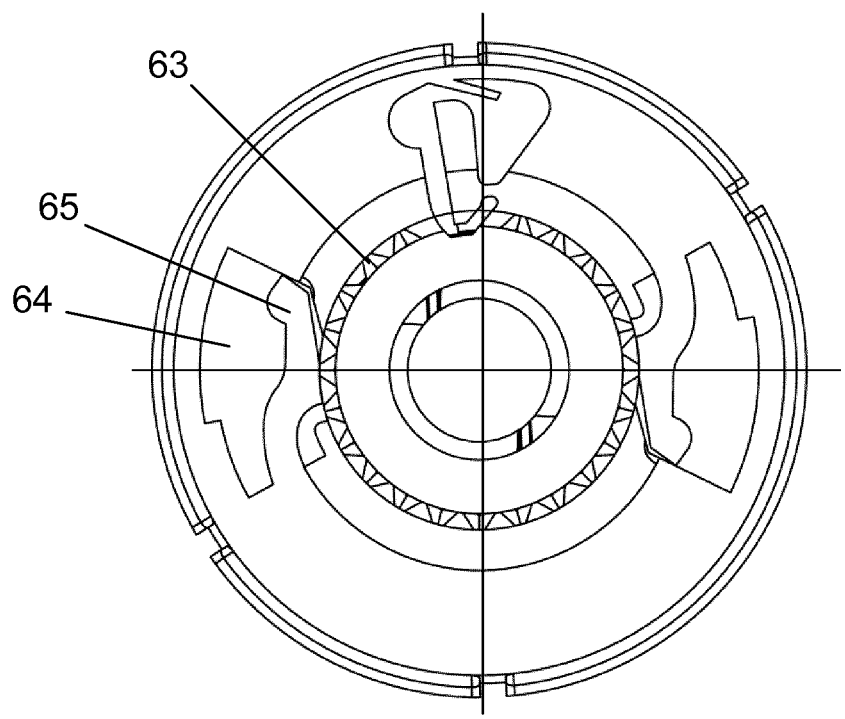
FIG. 11 Show an end-view of the nut assembly.
Figure 12:
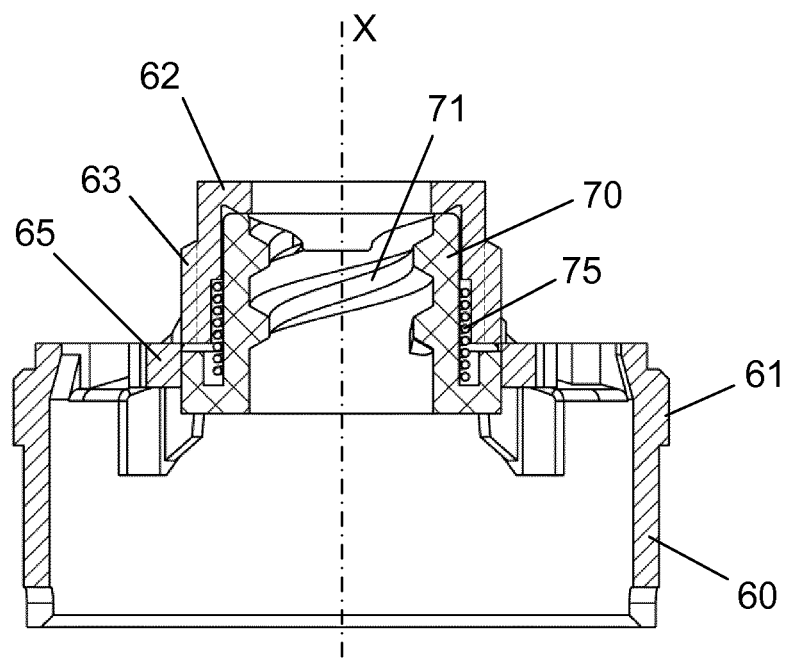
FIG. 12 show a cross sectional view of the nut assembly.

The nut holder 60 assembled with the nut member 70 is disclosed in details in the FIGS. 11-12, in which FIG. 11 is a top view of FIG. 12.

On the side, the nut holder 60 is provided with a number of protrusions 61 to secure the nut holder 60 relatively to the housing 2 both axially and rotational. Centrally the nut holder 60 is provided with a tower 62 which internally holds the nut member 70. This nut member 70 is rotational relatively to the nut holder 60 and a small torsion spring 75 is encompassed between the nut member 70 and the nut holder 60 to control the relative rotation between these two components 60, 70 as explained later.

Figure 13:
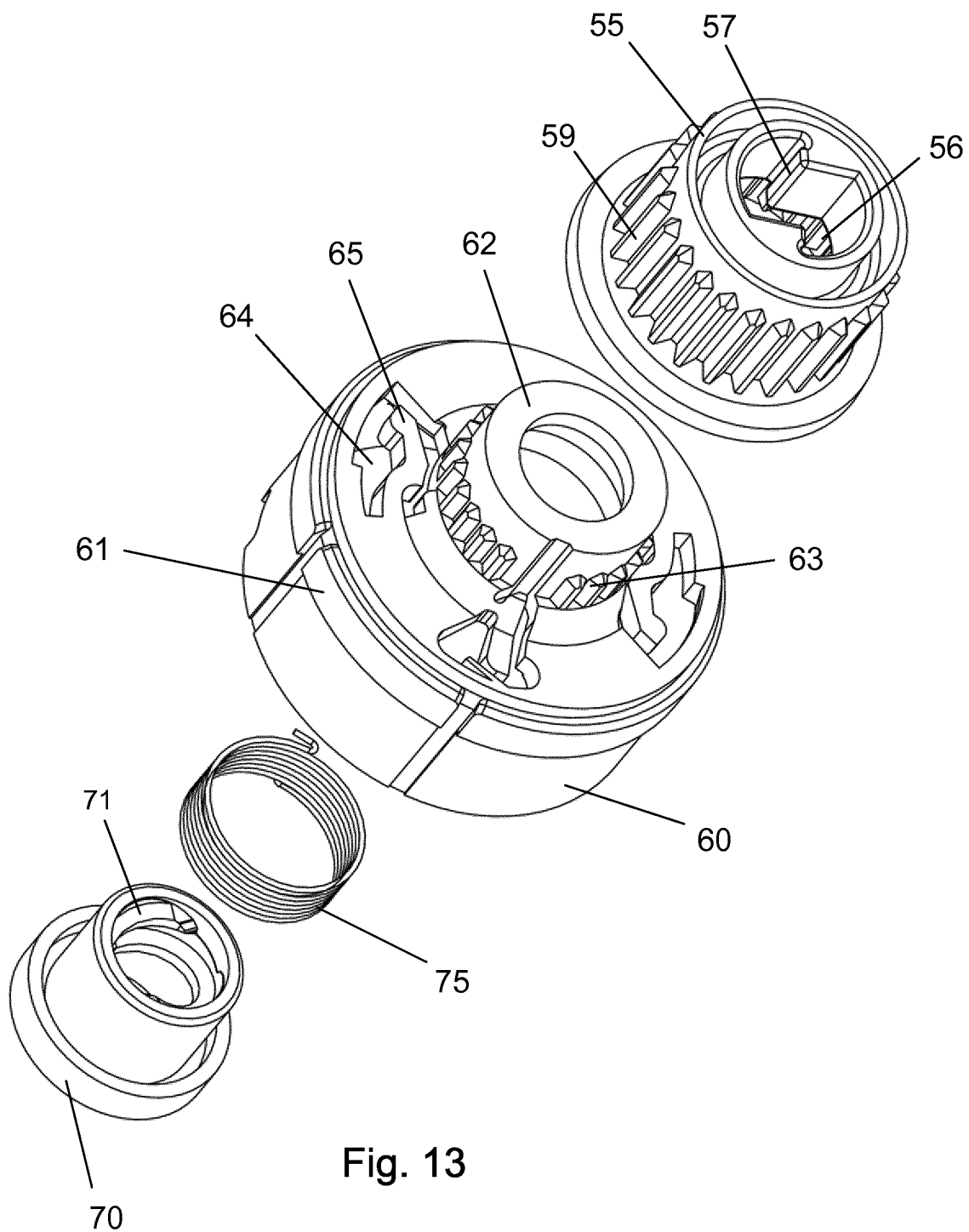
FIG. 13 show an exploded view of the drive assembly.

On the outside of the tower 62 a plurality of teeth 63 are provided. These teeth 63 engage similar teeth 56 provided internally in the drive member 55 (see e.g. FIG. 13). The drive member 55 is thus engaged with the nut holder 60 and thus with the housing 2, 3. Internally this drive member 55 is provided with a key 57 engaging the longitudinal groove 31 provided in the piston rod 30 such that whenever the drive member 55 is rotated, the piston rod 30 is forced rotated with the drive member 55.

Since the piston rod 30 on its outside surface is provided with a thread 32 engaging the internal thread 71 of the nut member 70, rotation of the piston rod 30 thus screws the piston rod 30 forward and further into the cartridge 10 thereby moving the plunger 12 in the distal direction.

The nut holder 60 is further provided with through-going openings 64 and a number of flexible arms 65 positioned within the boundaries of these openings 64.

Returning to FIG. 7-10 showing the drive mechanism of the injection device in different modes, FIG. 7 depicts the drive mechanism in the state of rest also disclosed in FIG. 1 and FIG. 5.

In all possible positions the nut holder 60 remains firmly connected to the housing 2, 3 or moulded integrally with the housing 2, 3, and the nut member 70 remains releasable connected to the nut holder 60.

Figure 9:
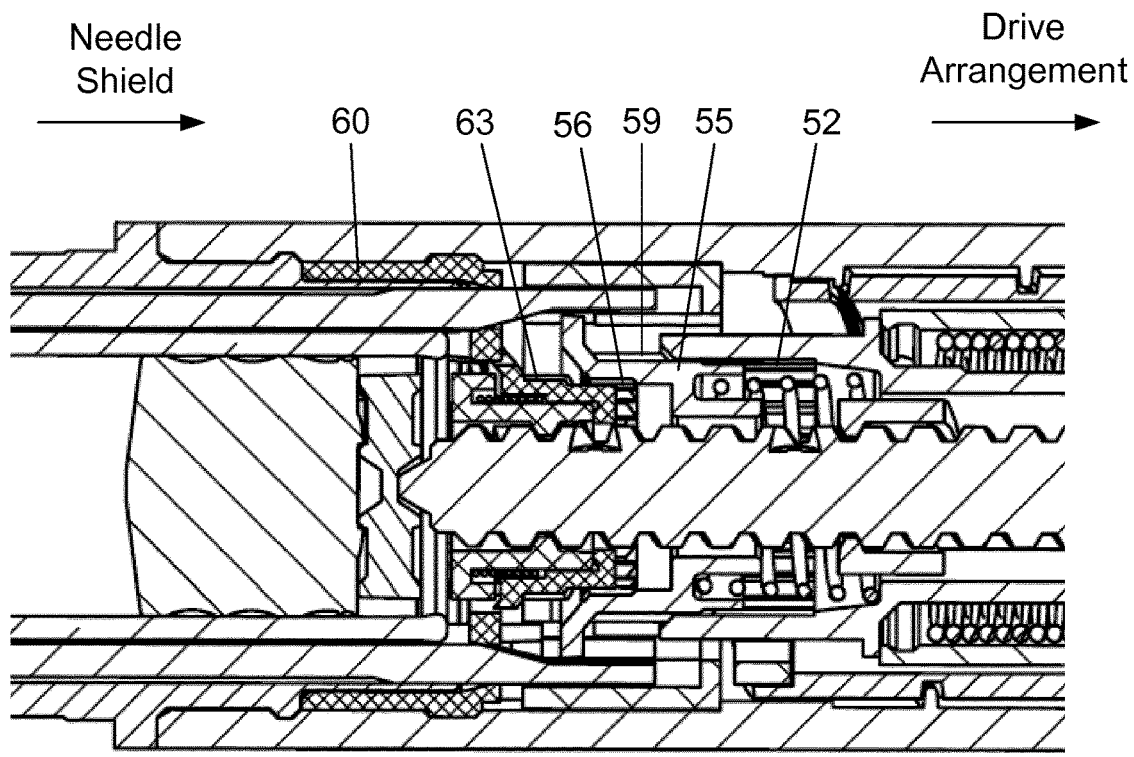
FIG. 9 show a cross sectional view of the drive mechanism with the needle shield activated.
Figure 10:
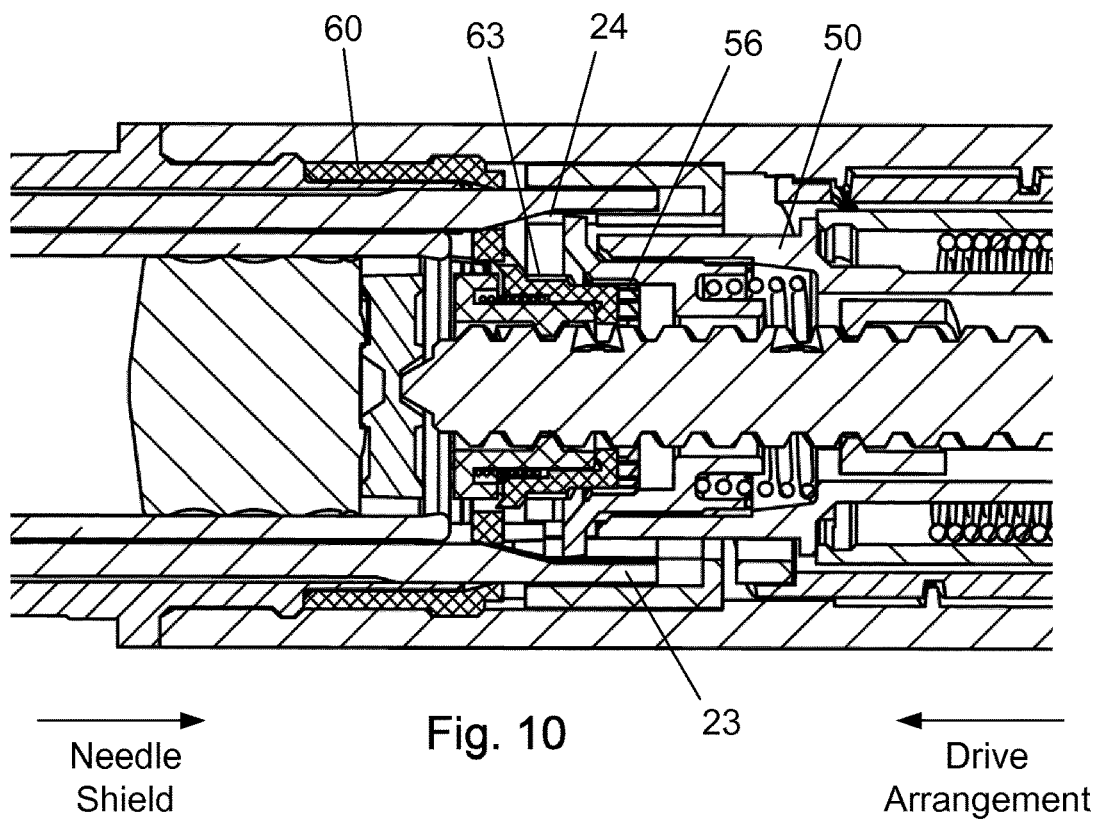
FIG. 10 show a cross sectional view of the drive mechanism during injection.

The needle shield 20 can be moved between a first extended position (depicted in FIG. 7-8) and a second retracted position (depicted in FIG. 9-10).

When the needle shield 20 is in its first extended position as depicted in FIG. 7-8, the drive member 55 is urged distally by the compression spring 58 provided between the drive member 55 and the drive arrangement 50. In this position, the teeth 56 provided internally in the drive member 55 engages the teeth 63 provided externally on the nut holder 60 thus preventing the drive member 55 from rotating.

When the telescopically movable needle shield 20 is shifted to its second position as depicted in FIG. 9-10, the arms 23 on the needle shield 20 moves the drive member 55 axially in the proximal direction. The arms 23 have steps 24 which engage a flange on the drive member 55 thus moving the drive member 55 axially. Once the drive member 55 is moved axially, the teeth 56 internally in the drive member 55 are released from the teeth 63 of the needle holder 60 such that the drive member 55 is free to rotate.

In the FIGS. 7 and 9, the drive arrangement 50 is in the third position which is the same position as depicted in FIG. 5 (and in FIG. 1). In this position, the drive arrangement 50 is locked to the dose dial 7 by the coupling 8 and the torque dialled into the torsion spring 35 is held by the ratchet mechanism 9. The result being that the rotation of the drive arrangement 50 in this position is transferred to torque in the torsion spring 35, however, since the ratchet 9 is a one way ratchet 9, this torque is unable to rotate the drive arrangement 50 when in the third position.

The drive arrangement 50 is distally provided with an internal toothing 52 supposed to engage with an external toothing 59 provided on an outside surface of the drive member 55.

In FIG. 7, neither the needle shield 20 nor the injection button 40 and the drive arrangement is activated. As a result, the drive member 55 is blocked from rotation by its engagement with the nut holder 60.

In FIG. 8, a user applies a pressure P onto the injection button 40 which moves the drive arrangement 50 in the distal direction such that the internal toothing 52 of the drive arrangement engages the external toothing 59 on the drive member 55. The drive arrangement 50 is further released from the dose dial 7 and thus set free to rotate under influence of the torsion spring 35, however as the drive member 55 remains in engagement with the nut holder 60, the drive member 55 is prevented for rotating and nothing happens.

FIG. 9 depicts the situation in which the needle shield 20 is activated to move in the proximal direction and the injection button 40 is not activated. In this position, the arms 23 of the needle shield 20 (via the steps 24) engage the drive member 55 and move the drive member 55 in the proximal direction such that the internal teeth 56 disengage the external teeth 63. In this position, the drive member 55 could potentially rotate, however since the injection button 40 is not moved, the drive arrangement 50 stays inrotatable connected to the dose dial 7.

In FIG. 10, the drive arrangement 50 is moved in the distal direction by the user activating the injection button 40. In this position the drive arrangement 50 is decoupled from the dose dial 7 such that the torsion spring 35 rotates the drive arrangement 50. At the same time the drive arrangement 50 is moved into engagement with the drive member 55 which again is decoupled from the nut holder 60 by the proximal movement of the shield arms 23. As a result, the drive member 55 rotates the piston rod 30 to rotate forward.

The below table relates to FIG. 7-10 and indicates the different positions of the needle shield 20 and of the drive arrangement 50. When the needle shield 20 is in its first extended position, the drive member 55 is locked relatively to the housing 2, however, when the needle shield 20 is moved to its second retracted position, the drive member 55 is disengaged.

Further, when the drive arrangement 50 is in its third position, the drive arrangement 50 is locked to the housing 2, and when the injection button 40 is pushed and the drive arrangement 50 moved into its fourth position, the drive arrangement 50 disengages the housing 2.

It is thus seen that the drive member 55 can only be freely rotated by the torsion spring 35 and the drive arrangement 50 when the needle shield 20 is in its second position and the drive arrangement 50 is in its fourth position. Rotation of the drive member 55 and the piston rod 30 thus requires both activation of the needle shield 20 and of the injection button 40, not necessarily simultaneously and not in any specific order, however both the injection button 40 and the needle shield 20 must be operated to release the set dose.

As disclosed in the FIGS. 11 to 15, the nut member 70 is rotatable mounted in the nut holder 60 which again is fixed in the housing 2 using the protrusions 61. This has the following function.

If the liquid drug inside the cartridge 10 is exposed to extreme cold the liquid will expand which moves the plunger 12 in the proximal direction. This proximal movement also moves the piston rod foot 33 proximally which again urges the piston rod 30 in the proximal direction. Since the nut member 70 is rotatable mounted in the nut holder 60 such proximal movement of the piston rod 30 will cause a rotation of the nut member 70.

A torsion spring 75 is provided between the nut member 70 and the nut holder 60 which torsion spring 75 is strained as the nut member 70 rotate.

When the liquid drug is warmed up e.g. when the injection device is removed from a refrigerator and kept at room temperature, the liquid drug will retract its volume and thus draw the plunger 12 in a distal direction. When the plunger 12 thus moves distally, the piston rod foot 33 and the piston rod 30 will follow since the torsion spring 75 will unstrain and thus rotate the nut member 70.

The rotatable nut member 70 thus provides a so-called pressure-relief system which makes sure that the piston rod foot 33 (and the piston rod 30) always stay abut with the plunger 12.

However, in order to eject the set dose, the piston rod 30 needs to rotate. Such rotation can only be established if the nut member 70 is locked to the housing 2, 3 at least during ejection. Therefore the disclosed pressure-relief system requires an element which locks the nut member 70 to the housing 2, 3 when ejecting.

Figure 15:
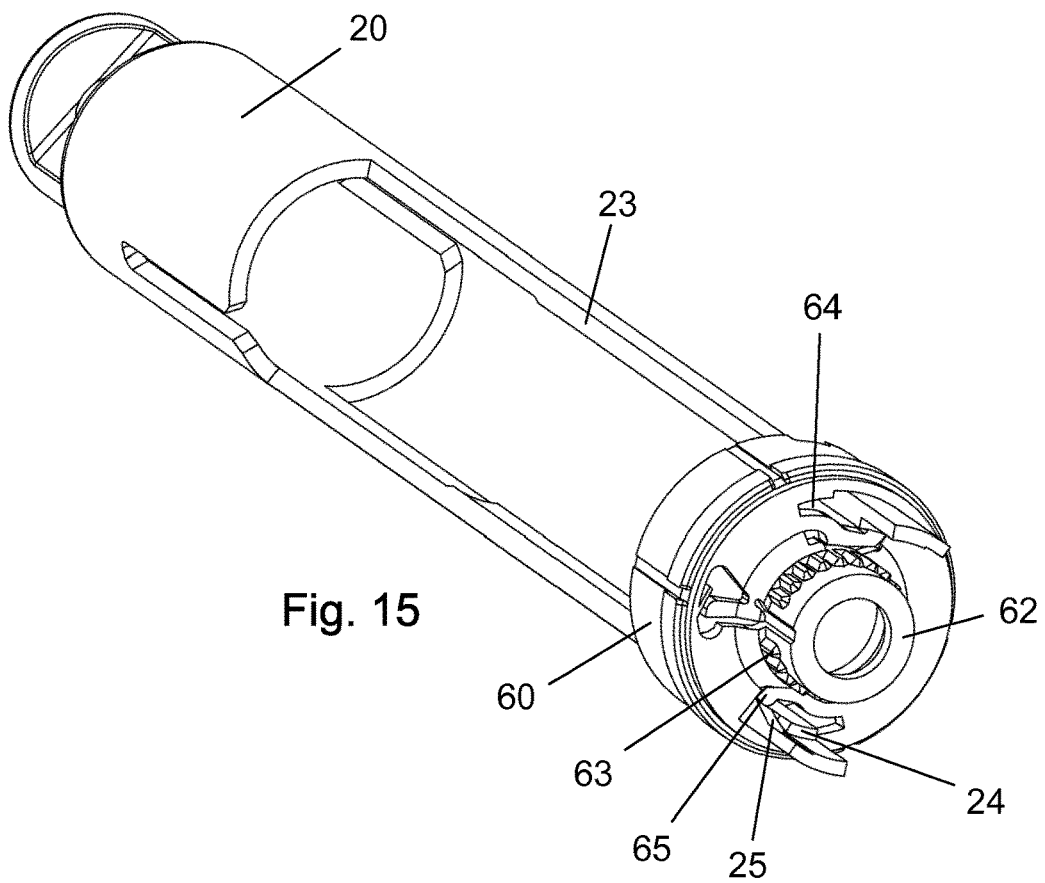
FIG. 15 show a different perspective view of the telescopically movable needle shield viewed from a proximal position.

In this particular case, the arms 23 of the needle shield 20 are provided with a ramp 25 which during ejection is moved in a proximal direction. During this movement, this ramp 25 engages radial arms 65 provided in the nut holder 60 as best seen in FIG. 15. The ramp 55 presses these arms 65 in a radial direction into abutment with the nut element 70 which thereby locks the nut member 70 to the nut holder 60.

In the situation disclosed in FIG. 9-10 where the needle shield 20 is moved to its retracted position, the ramp 25 presses the arms 65 against an outer surface of the nut member 70 thus locking the nut holder 70 to the housing 2.

| Needle shield 20 in: | First position (FIG. 7 + 8) Drive member 55 locked to housing. | Second position (FIG. 9 + 10) Drive member 55 unlocked from housing. |
|---|---|---|
| Drive arrangement 50 in: | | |
| Third position (FIG. 7 + 9) | Drive arrangement 50 locked to housing (FIG. 7). | Drive arrangement 50 locked to housing (FIG. 9). |
| Fourth position (FIG. 8 + 10) | Drive arrangement 50 unlocked from housing (FIG. 8). | Drive arrangement 50 unlocked from housing (FIG. 10). |

Table relating to FIGS. 7, 8, 9 and 10.

It is evident that this pressure-relief system can be provided in any injection device having a telescopically movable needle shield 20. The primary objective simply being that the nut member 70 is locked to housing 2 when the needle shield 20 is retracted during injection.

How the dose itself is released has no influence on the pressure-relief system.

It is also evident, that the herein described release system requiring activation of both the needle shield 20 and the injection button 40 can be realized both with this pressure-relief system or without the pressure-relief system. In the latter case, the thread 71 can be formed as an integral part of the nut holder 60, thus avoiding both the rotatable nut member 70 and the torsion spring 75.

Some preferred embodiments have been shown in the foregoing, but it should be stressed that the invention is not limited to these, but may be embodied in different ways within the subject matter as defined in the following claims.

The invention claimed is:

1. A torsion spring driven injection device for delivering set doses of a liquid drug, comprising:
    a housing storing a cartridge containing a liquid drug,
        a needle cannula in liquid communication with the interior of the cartridge and having a distal tip shielded by a telescopically movable needle shield, wherein the needle shield is axially movable from a first position in which the needle shield is extended to cover the distal tip of the needle cannula to a second position in which the needle shield is retracted to expose the distal tip of the needle cannula,
    a piston rod having a threaded outer surface and a noncircular cross-section, for driving the liquid drug out from the cartridge through the needle cannula,
    a rotatable dose setting member by which a user can set the size of a dose to be injected,
    a torsion spring which is strainable in response to the user rotating the dose setting member and releasable to drive the piston rod, and
    a user operable injection button, activation of which releases the torsion spring,
    a rotatable drive member mating with the noncircular cross-section of the piston rod or having an inner thread mating with the outer thread of the piston rod, and
    a nut member releasably coupled to the housing and having an inner thread mating with the outer thread of the piston rod or having a cross-section mating with the noncircular cross-section of the piston rod, such that the piston rod is moved axially in the housing upon rotation of the drive member relative to the housing, wherein
the needle shield is configured to lock the nut member to the housing upon telescopic movement of the needle shield from the first position to the second position.

2. A torsion spring driven injection device according to claim 1, wherein the nut member is unlocked from the housing upon telescopic movement of the needle shield from the second position to the first position.

3. A torsion spring driven injection device according to claim 1, wherein a plurality of radially working arms are provided in the housing or in a part connected to the housing.

4. A torsion spring driven injection device according to claim 3, wherein the needle shield activates the radially working arms to lock the nut to the housing or to the nut holder when the needle shield is moved to the second position.

5. A torsion spring driven injection device according to claim 1, wherein the torsion spring is encompassed between the housing and a drive arrangement, wherein the drive arrangement is adapted to rotate the rotatable drive member under influence of the torque of the torsion spring.

6. A torsion spring driven injection device according to claim 5, wherein the drive member is releasably coupled to the drive arrangement.

7. A torsion spring driven injection device according to claim 5, wherein the drive arrangement is coupled to the injection button such that the drive arrangement follows axial movement of the injection button.

8. A torsion spring driven injection device according to claim 5, wherein the drive member engages to the housing.

9. A torsion spring driven injection device according to claim 5, wherein the drive member is axially movable to disengage from the housing.

10. A torsion spring driven injection device according to claim 9, wherein the drive member is axially movable by the needle shield such that the drive member is movable out of engagement with the housing upon movement of the needle shield from the first position to the second position.

11. A torsion spring driven injection device according claim 5, wherein the drive arrangement is axially movable in relation to the housing from a third position to a fourth position upon axial movement of the injection button.

12. A torsion spring driven injection device according to claim 11, wherein the drive arrangement in the third position is coupled to the housing and cannot be rotated, and in the fourth position is decoupled from the housing so that it may rotate under the influence of the torsion spring.

13. A torsion spring driven injection device according to claim 11, wherein the drive arrangement in the third position is decoupled from the drive member and in the fourth position is coupled to drive member.

14. A torsion spring driven injection device according to claim 11, wherein rotation of the rotatable drive member by the torsion spring requires;
    the needle shield to be in the second position thus releasing the rotatable drive member from the housing, and
    the drive arrangement to be in the fourth position thus delivering the torque of the torsion spring to the rotational drive member via the drive arrangement.

15. A torsion spring driven injection device according to claim 1, wherein the needle shield carries a cleaning chamber for cleaning the distal tip of the needle cannula between subsequent injections.

16. A torsion spring driven injection device according to claim 3, wherein the plurality of radially working arms provided in the housing or in a part connected to the housing comprises a nut holder secured to the housing.

* * * * *